United States Patent [19]

Miesel et al.

[11] 3,939,166

[45] Feb. 17, 1976

[54] 4-SUBSTITUTED-5-CYANO-7-NITRO-2-($\alpha,\alpha$-DIFLUOROALKYL)BENZIMIDAZOLES

[75] Inventors: John L. Miesel; David I. Wickiser, both of Indianapolis, Ind.

[73] Assignee: Eli Lilly and Company, Indianapolis, Ind.

[22] Filed: Nov. 15, 1973

[21] Appl. No.: 416,298

Related U.S. Application Data

[62] Division of Ser. No. 232,289, March 6, 1972, abandoned.

[52] U.S. Cl. ........... 260/293.6; 260/309.2; 424/267; 424/273
[51] Int. Cl.$^2$........................................ C07D 235/16
[58] Field of Search ......... 511/232, 289; 260/309.2, 260/293.6

[56] References Cited
UNITED STATES PATENTS

| | | | |
|---|---|---|---|
| 3,418,318 | 12/1968 | Lambie et al. | 260/247.5 |
| 3,528,798 | 9/1970 | Pfeiffer | 71/92 |

*Primary Examiner*—G. Thomas Todd
*Attorney, Agent, or Firm*—Kathleen S. Page; Everet F. Smith

[57] ABSTRACT

4,5-Disubstituted-7-nitro-2-($\alpha,\alpha$-difluoroalkyl)benzimidazole compounds and their alkali metal and alkaline earth metal salts, useful as insecticides.

9 Claims, No Drawings

4-SUBSTITUTED-5-CYANO-7-NITRO-2-(<,<-DIFLUOROALKYL)BENZIMIDAZOLES

This is a division of application Ser. No. 232,289, filed Mar. 6, 1972, now abandoned.

SUMMARY OF THE INVENTION

The present invention is directed to compounds of the formula

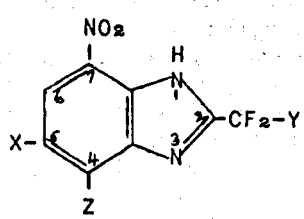

wherein X represents cyano or trifluoromethyl; wherein Y represents
a. hydrogen,
b. chlorine,
c. fluorine,
d. trifluoromethyl, or
e. pentafluoroethyl;
and wherein Z represents a

wherein, when each of $R^0$ and $R^1$ is taken separately, each independently represents, subject to the limitation that at least one of $R^0$ and $R^1$ contains more than 1 carbon atom and that $R^0$ and $R^1$ together contain less than 9 carbon atoms;
1. hydrogen,
2. alkyl,
3. alkenyl containing more than 2 carbon atoms,
4. alkynyl containing more than 2 carbon atoms,
5. (fluoroalkyl)methyl wherein alkyl is $C_1$–$C_7$, both inclusive, and bears at least one fluorine atom,
6. cycloalkyl of $C_3$–$C_8$, both inclusive,
7. cycloalkylloweralkyl, wherein cycloalkyl is of $C_3$–$C_6$, both inclusive, and loweralkyl is of $C_1$–$C_4$, both inclusive, or
8. loweralkylcycloalkyl, wherein cycloalkyl and loweralkyl are as defined in the preceding candidate moiety;

or when $R^0$ and $R^1$ are taken together, they jointly constitute, with the nitrogen atom to which they are attached, piperidino; or b. —$R^2$—$R^3$ wherein $R^2$ represents oxygen or sulfur, and $R^3$ represents
1. alkyl of $C_1$–$C_8$, both inclusive,
2. alkenyl of $C_3$–$C_8$, both inclusive,
3. alkynyl of $C_3$–$C_8$, both inclusive,
4. (fluoroalkyl)methyl wherein alkyl is $C_1$–$C_7$, both inclusive, and bears at least one fluorine atom,
5. cycloalkyl of $C_3$–$C_6$, both inclusive,
6. cycloalkylloweralkyl, wherein cycloalkyl is of $C_3$–$C_6$, both inclusive, and loweralkyl is of $C_1$–$C_4$, both inclusive, or
7. loweralkylcycloalkyl, wherein cycloalkyl and loweralkyl is as defined in the preceding candidate moiety, or c. primary loweralkyl of $C_1$–$C_4$;
and the alkali metal and alkaline earth metal salts thereof.

The above-described compounds exhibit insecticidal activity; hence, the present invention is also directed to insecticidal methods employing, and compositions comprising, the above-described compounds. In addition, certain of the compounds exhibit herbicidal activity.

DETAILED DESCRIPTION OF THE INVENTION

Formulae employed throughout the present specification are predicated on the assumption that the proton on the imidazole portion of the benzimidazole ring is affixed at a ring position arbitrarily designated as 1:

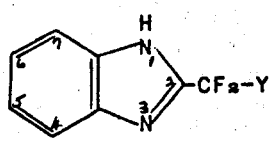

However, this proton may not be attached to a specific ring nitrogen atom. Rather, it is believed that the compounds typically exist as tautomers, e.g.:

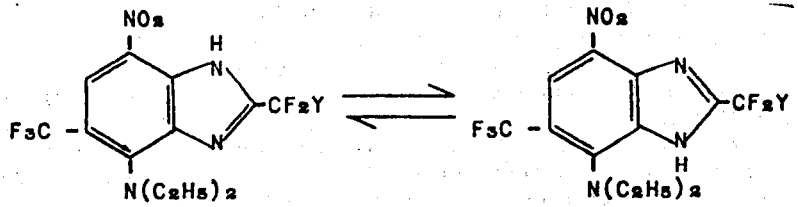

Therefore, the formulae herein, while showing the proton fixably positioned for the sake of uniform representation, are employed to designate either of the tautomeric forms or the more typical tautomeric mixture.

The compounds of the present invention are typically crystalline solids. Except for the compounds wherein Z represents primary loweralkyl, they are prepared by reacting a 4-halo-5-substituted-7-nitro-2-($\alpha,\alpha$-difluoroalkyl)benzimidazole of the formula

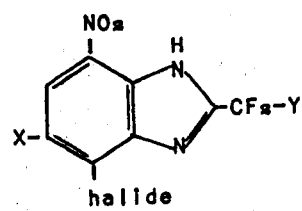

wherein halide is bromide or chloride, with a reactant, the identity of which varies with the identity of the desired product. For the compounds wherein Z represents an amino group, the reactant is a compound of the formula

and the reaction is carried out in the presence of a hydrogen halide acceptor, which can be any tertiary amine or an additional portion of the amine reactant. For the compounds wherein Z represents an alkoxy or alkylthio group, the reactant is an alkali metal derivative of the corresponding alcohol or mercaptan. Regardless of the identity of the particular reactants, the reaction is conveniently conducted in an inert liquid reaction medium, and goes forward over a wide range of temperatures, such as from room temperature to reflux temperatures.

In carrying out the reaction, the reactants, or reactants and hydrogen halide acceptor, are contacted with one another in the reaction medium. The reaction goes forward readily, yielding some of the desired 4,5-disubstituted-7-nitro-2-(α,α-difluoroalkyl)benzimidazole product and amine hydrogen halide by-product or alkali metal halide by-product at once; however, it is generally preferred to hold the reaction mixture for a period of time to insure maximum yields. Temperatures higher than room temperatures, such as reflux temperatures, are often preferred. In the case of compounds which present steric hindrance, higher temperatures, pressures in excess of atmospheric pressure, and specialty solvents, such as hexamethylphosphoramide, may be useful in obtaining good yields.

The product of the reaction can be separated from the reaction mixture by conventional methods. Typically, the by-product salt precipitates in the reaction mixture and is removed by filtration and solvent thereafter removed by evaporation to separate the desired product as a residue. Such product residue can be purified, if desired, in conventional procedures, typically recrystallization.

In the instance of compounds wherein Z represents primary loweralkyl another reaction route is necessary. This route is schematically described as follows, wherein $R^4$ represents hydrogen or alkyl of no more than 3 carbon atoms:

elevated temperatures offer no advantage, room temperatures are preferred. The resulting product, the 4-(bis(carboethoxy)methyl)-5-substituted-7-nitro-2-(α,α-difluoroalkyl)benzimidazole, as such or as its potassium salt, is separated in conventional procedures and thereafter deesterified and decarboxylated. This is conveniently achieved by reacting the product of the preceding reaction with sulfuric acid, preferably at a temperature of about 100°C. The resulting product, 4-(carboxymethyl)-5-substituted-7-nitro-2-(α,α-difluoroalkyl)benzimidazole, is then reacted with base, conveniently sodium bicarbonate in dimethylformamide. The reaction is preferably carried out at temperatures of about 50°–100°C., most preferably at temperatures of about 70°–80°C. Separation and, if desired, purification, are carried out in conventional procedures.

Those compounds of the present invention which are alkali metal and alkaline earth metal salts are prepared by reacting the compounds of the present invention whose preparation is described above

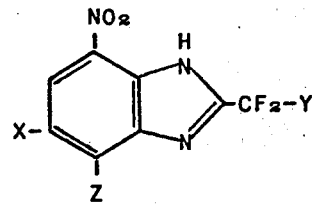

with an alkali metal alkoxide or an alkaline earth oxide. The reaction goes forward under temperatures of a wide range, such as from 20° to 120°C. An inert liquid reaction medium is necessary for good results; the loweralkanols are especially suitable for this purpose.

In carrying out the reaction, the reactants and solvent are contacted with one another in any way, and the resulting reaction mixture maintained in the reaction temperature range for a period of time. Solvents and by-product loweralkanol are then removed, conveniently by evaporation under subatmospheric pressure, to obtain the desired product as a residue. Purification can be carried out in conventional procedures if desired, typically by recrystallization.

The following examples illustrate the synthesis of the

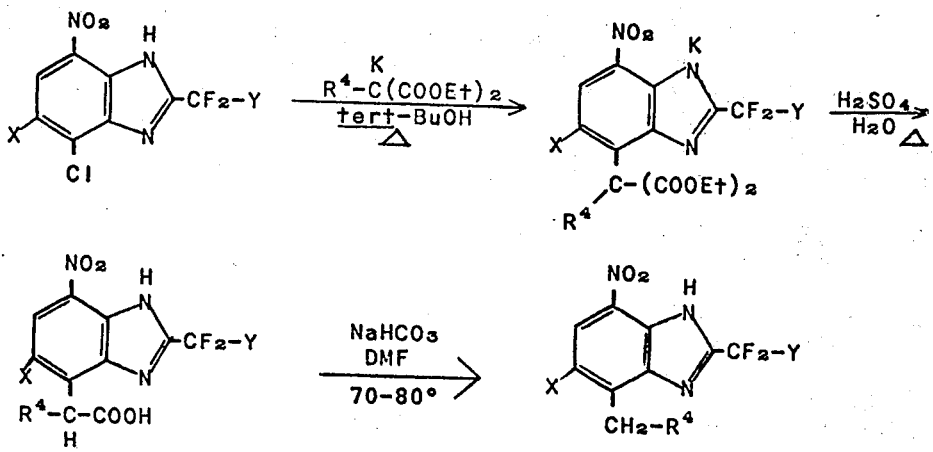

Each individual reaction is conducted in accordance with conventional procedures.

More particularly, the initial reaction of 4-halo-5-substituted-7-nitro-2-(α,α-difluoroalkyl)benzimidazole with the potassium diethyl malonate is conveniently conducted in an inert liquid, such as tert-butanol, and goes forward over a wide range of temperatures. Since compounds of the present invention and will enable those skilled in the art to practice the present invention.

EXAMPLE 1:

4-PROPYLAMINO-7-NITRO-2,5-BIS(TRIFLUOROMETHYL)BENZIMIDAZOLE

4-Chloro-7-nitro-2,5-bis(trifluoromethyl)benzimidazole (2.2 grams), propylamine (0.39 gram), and excess triethylamine were mixed in about 50 milliliters of ethanol. The reaction mixture was heated to reflux and refluxed over a weekend (about 60 hours). The reaction mixture was then poured into water and acidified. The desired 4-propylamino-7-nitro-2,5-bis(trifluoromethyl)benzimidazole product precipitated and was separated by filtration. After recrystallization from a mixture of ethanol and water, the compound melted at 129°–31°C. Analysis, Calc.: C, 40.4; H, 2.81; N, 15.73 Found: C, 40.5; H, 2.78; N, 15.51

EXAMPLE 2:
4-ETHOXY-7-NITRO-2,5-BIS(TRIFLUOROMETHYL)BENZIMIDAZOLE

4-Chloro-7-nitro-2,5-bis(trifluoromethyl)benzimidazole (3.0 grams; 0.09 mole) was added to about 100 milliliters of ethanol, and the mixture was then refluxed overnight (3.0 grams) and the starting material was recovered. Sodium (.42 gram; 0.018 mole) was added to 100 milliliters of ethanol, and the recovered 4-chloro-7-nitro-2,5-bis(trifluoromethyl)benzimidazole was added at room temperature and the resulting reaction mixture was stirred at room temperature over a weekend. TLC showed only the starting material, so the reaction mixture was heated to reflux and refluxed overnight. The reaction mixture was then poured into water, acidified, and extracted with ethyl acetate. The extract was dried over magnesium sulfate and solvent removed by evaporation to obtain the desired 4-ethoxy-7-nitro-2,5-bis(trifluoromethyl)benzimidazole. After recrystallization from a mixture of ethanol and water, it melted at 144°–46°C. Analysis, Calc.: C, 38.50; H, 2.06; N, 12.24 Found: C, 38.65; H, 2.26; N, 12.36

EXAMPLES 3–13:

Ohter representative products of the present invention, prepared according to the foregoing teachings and examples, are set forth in the following table.

TABLE I

| X | Y | Z | Characterizing Property |
|---|---|---|---|
| $CF_3$ | $CF_3$ | ethoxy | m.p., 123–25°C. |
| $CF_3$ | $CF_3$ | propoxy | m.p., 90–92°C. |
| CN | F | ethoxy | m.p., 193–97°C. |
| $CF_3$ | F | methoxy | m.p., 143–45°C. |
| $CF_3$ | F | ethylthio | m.p., 134–36°C. |
| $CF_3$ | F | piperidino | m.p., 157–58°C. |
| $CF_3$ | F | butylamino | m.p., 135–36°C. |
| $CF_3$ | F | cyclohexylamino | m.p., 134–35°C. |
| $CF_3$ | F | sec-butylamino | m.p., 109–11°C. |
| CN | F | propylamino | m.p., 228–30°C. |
| CN | $CF_3$ | piperidino | m.p., 216–19°C. |

EXAMPLES 14–46:

Yet other representative compounds of the present invention, prepared in accordance with the foregoing teaching and examples, include the following:

4-Chloro-7-nitro-2,5-bis(trifluoromethyl)benzimidazole is reacted with the sodium salt of 3-hexene-1-thiol to obtain 4-(3-hexenylthio)-7-nitro-2,5-bis(trifluoromethyl)-benzimidazole, m.w., 413.4.

4-Chloro-7-nitro-5-trifluoromethyl-2-difluoromethylbenzimidazole is reacted with sec-butylamine to obtain 4-secbutylamino-7-nitro-5-trifluoromethyl-2-difluoromethylbenzimidazole, m.w., 352.3.

4-Chloro-7-nitro-5-cyano-2-difluorochloromethylbenzimidazole is reacted with diallylamine, to obtain 4-(diallylamino)-7-nitro-5-cyano-2-difluorochloromethylbenzimidazole, which when reacted with sodium methoxide yields the corresponding sodium salt, m.w., 389.7.

4-Chloro-7-nitro-5-trifluoromethyl-2-pentafluoroethylbenzimidazole is reacted with 3-hexenylamine to obtain 4-(3-hexenylamino)17-nitro-5-trifluoromethyl-2-pentafluoroethylbenzimidazole, m.w., 446.3.

4-Chloro-7-nitro-2,5-bis(trifluoromethyl)benzimidazole is reacted with 2-propynylamine to obtain 4-(2-propynylamino)-7-nitro-2,5-bis(trifluoromethyl)benzimidazole, m.w., 352.2.

4-Chloro-7-nitro-5-trifluoromethyl-2-difluorochloromethylbenzimidazole is reacted with 2,2,2-trifluoroethylamine to obtain 4-(2,2,2-trifluoroethylamino)-7-nitro-5-trifluoromethyl-2-difluorochloromethylbenzimidazole, m.w., 412.7.

4-Chloro-7-nitro-5-cyano-2-pentafluoroethylbenzimidazole is reacted with 2-cyclohexylethylamine to obtain 4-(2-cyclohexylethylamino)-7-nitro-5-cyano-2-pentafluoroethylbenzimidazole, m.w., 329.3.

4-Chloro-7-nitro-2,5-bis(trifluoromethyl)benzimidazole is reacted with 2-methylcyclohexylamine to obtain 4-(2-methylcyclohexylamino)-7-nitro-2,5-bis(trifluoromethyl)-benzimidazole, which is reacted with potassium ethoxide to yield the corresponding potassium salt, m.w., 448.4.

4-Chloro-7-nitro-5-cyano-2-difluoromethylbenzimidazole is reacted with the sodium salt of allyl alcohol to obtain 4-allyloxy-7-nitro-5-cyano-2-difluoromethylbenzimidazole, m.w., 294.2.

4-Chloro-7-nitro-5-cyano-2-difluorochloromethylbenzimidazole is reacted with the potassium salt of 2-propynel-thiol to obtain 4-(2-propynylthio)-7-nitro-5-cyano-2-difluorochloromethylbenzimidazole, m.w., 342.7.

4-Chloro-7-nitro-5-trifluoromethyl-2-heptafluoropropylbenzimidazole is reacted with sec-butylamine to obtain 4-sec-butylamino-7-nitro-5-trifluoromethyl-2-heptafluoropropylbenzimidazole, m.w., 470.3.

4-Chloro-7-nitro-5-cyano-2-pentafluoroethylbenzimidazole is reacted with the sodium salt of 2,2,2,-trifluoroethanol to obtain 4-(2,2,2-trifluoroethoxy)-7-nitro-5-cyano-2-pentafluoroethylbenzimidazole, m.w., 404.2.

4-Chloro-7-nitro-2,5-bis(trifluoromethyl)benzimidazole is reacted with the sodium sale of cyclohexanol to obtain 4-cyclohexyloxy-7-nitro-2,5-bis(trifluoromethyl)benzimidazole, m.w., 397.3.

4-Chloro-7-nitro-5-cyano-2-difluoromethylbenzimidazole is reacted with the sodium salt of cyclopentanethiol to obtain 4-cyclopentylthio-7-nitro-5-cyano-2-difluoromethylbenzimidazole, m.w., 338.3.

4-Chloro-7-nitro-5-trifluoromethyl-2-difluorochloromethylbenzimidazole is reacted with the sodium salt of 2-methyl-1-cyclopentanol to obtain 4-(2-methylcyclopentyloxy)-7-nitro-5-trifluoromethyl-2-difluorochloromethylbenzimidazole, m.w., 385.7.

4-Chloro-7-nitro-2,5-bis(trifluoromethyl)benzimidazole is reacted with the sodium salt of 2-cyclopentylethanol to obtain 4-(2-cyclopentylethoxy)-7-nitro-2,5-bis(trifluoromethyl)benzimidazole, m.w., 397.3.

4-Chloro-7-nitro-2,5-bis(trifluoromethyl)benzimidazole is reacted with potassium diethyl malonate to obtain 4-(bis(carboethoxy)methyl)-7-nitro-2,5-bis(- trifluoromethyl)-benzimidazole; this intermediate is deesterified and decarboxylated to yield 4-methyl-7-nitro-2,5-bis(trifluoromethyl)-benzimidazole, m.w., 313.2. In like procedures, the following are prepared:

4-ethyl-7-nitro-5-cyano-2-difluorochloromethylbenzimidazole, which is reacted with sodium methoxide to obtain the corresponding sodium salt, m.w., 322.6;

4-propyl-7-nitro-5-trifluoromethyl-2-difluoromethylbenzimidazole, m.w., 323.2;

4-isobutyl-7-nitro-5-trifluoromethyl-2-pentafluoroethylbenzimidazole, which is reacted with potassium methoxide to obtain the corresponding potassium salt, m.w., 443.4; and 4-butyl-7-nitro-5-cyano-2-heptafluoropropylbenzimidazole, m.w., 412.3.

4-Chloro-7-nitro-5-cyano-2-trifluoromethylbenzimidazole is reacted with piperidine to obtain 4-piperidino-7-nitro-5-cyano-2-trifluoromethylbenzimidazole, m.w., 339.3. This compound is reacted with calcium oxide to obtain the corresponding calcium salt, m.w., 716.6.

4-Chloro-7-nitro-2,5-bis(trifluoromethyl)benzimidazole is reacted with the sodium salt of 3,3,3-trifluoropropanel-thiol to obtain 4-(3,3,3-trifluoropropylthio)-7-nitro-2,5-bis(trifluoromethyl)benzimidazole, m.w., 427.3.

4-Chloro-7-nitro-2,5-bis(trifluoromethyl)benzimidazole is reacted with cyclopropylamine to obtain the corresponding 4-(cyclopropylamino)-7-nitro-2,5-bis(trifluoromethyl)-benzimidazole, m.w., 354.2.

4-Chloro-7-nitro-2,5-bis(trifluoromethyl)benzimidazole is reacted with dibutylamine to obtain 4-(dibutylamino)-7-nitro-2,5-bis(trifluoromethyl)benzimidazole, m.w., 426.4.

4-Chloro-7-nitro-5-cyano-2-trifluoromethylbenzimidazole is reacted with N-methylcyclopentylamine to obtain 4-(N-methylcyclopentylamino)-7-nitro-5-cyano-2-trifluoromethylbenzimidazole, m.w., 353.3.

4-Chloro-7-nitro-5-cyano-2-trifluoromethylbenzimidazole is reacted with the sodium derivative of 1-octanol to obtain 4-octyloxy-7-nitro--cyano-2-trifluoromethylbenzimidazole, m.w., 384.4.

4-Chloro-7-nitro-2,5-bis(trifluoromethyl)benzimidazole is reacted with the potassium derivative of tertbutanethiol to obtain 4-(tert-butylthio)-7-nitro-2,5-bis-(trifluoromethyl)benzimidazole, m.w., 387.3.

4-Chloro-7-nitro-5-cyano-2-trifluoromethylbenzimidazole is reacted with cyclopentanemethylamine to obtain 4-cyclopentanemethylamino-7-nitro-5-cyano-2-trifluoromethylbenzimidazole, m.w., 353.3.

4-Chloro-7-nitro-2,5-bis(trifluoromethyl)benzimidazole is reacted with cyclopropanepropylamine to obtain 4-cyclopropanepropylamino-7-nitro-2,5-bis(trifluoromethyl)-benzimidazole, m.w., 396.3.

4-Chloro-7-nitro-5-cyano-2-trifluoromethylbenzimidazole is reacted with 2-ethylcyclobutylamine to obtain 4-((2-ethylcyclobutyl)amino)-7-nitro-5-cyano-2-trifluoromethylbenzimidazole, m.w., 353.3.

4-Chloro-7-nitro-2,5-bis(trifluoromethyl)benzimidazole is reacted with 2-octyn-1-ylamine to obtain 4-(2-octyn-1ylamino)-7-nitro-2,5-bis(trifluoromethyl)-benzimidazole, m.w., 422.3.

4-Chloro-7-nitro-5-cyano-2-pentafluoroethylbenzimidazole is reacted with the sodium derivative of 4-hexyn-2-ol to obtain 4-(1-methyl-3-pentyn-1-yloxy)-7-nitro-5-cyano-2-pentafluoroethylbenzimidazole, m.w., 402.3.

The compounds of the present invention are useful for the control of insect and arachnid pests and can be used for the control of those insect and arachnid pests found on the roots or aerial portion of plants. These compounds are active, for example, against such arachnids as red spider mite, citrus mite, two-spotted spider mite, Pacific mite, clover mite, fowl mite, various species of ticks, and various species of spiders. The compounds are also active against insects of the various orders including Mexican bean beetle, bollweevil, corn rootworm, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, pea aphid, mealybugs, scales, leafhoppers, citrus aphid, spotted alfalfa aphid, green peach aphid, bean aphid, milkweed bug, tarnished plant bug, box elder bug, and bed bug, squash bug, chinch bug, house fly, yellow fever mosquito, stable fly, horn fly, cabbage maggot, carrot rust fly, Southern armyworm, codling moth, cutworm, clothes moth, Indianmeal moth, leaf-rollers, corn earworm, European corn borer, cabbage looper, cotton bollworm, bagworm, sod webworm, fall armyworm, German cockroach, and American cockroach.

In addition to utilization for the control of pests on plants, the compounds of this sub-genus of the present invention can also be included in inks, adhesives, soaps, polymeric materials, cutting oils or in oil or latex paints. Also, the products can be distributed in textiles, cellulose materials, or in grains, or can be employed in the impregnation of wood and lumber. Additionally, they can be applied to seeds. In yet other procedures, the products can be vaporized or sprayed or distributed as aerosols into the air, or onto surfaces in contact with the air. In such applications, the compounds manifest the useful properties hereinbefore described.

The methods of the present invention comprise contacting an insect or arachnid with an inactivating amount of one of the compounds of the present invention. Contacting can be affected by application of one or more of the products to a habitat of the insect or arachnid. Representative habitats include soil, air, water, food, vegetation, inert objects, stored matter such as grains, other animal organism, and the like. The inactivation can be lethal, immediately, or with delay, or can be a sub-lethal one in which the inactivated insect or arachnid is rendered incapable of carrying out one or more of its normal life processes. Among known insecticides, this latter situation typically prevails when one of the systems of the organism, often the nervous system, is seriously distrubed; however, the precise mechanism by which the compounds constituting the present active agent work is not yet known, and the insecticidal and arachnicidal method of the present invention is not limited by any mode of operation.

The utilization of an inactivating amount of one of the compounds of the present invention is critical to the insecticidal and arachnicidal method of the present invention. The inactivating amount can sometimes be administered by employing the compound in unmodified form. However, for good results, it is generally necessary that the compound or compounds be employed in modified form, that is, as one component of a composition formulated to implement the arachnicidal and insecticidal effects. Thus, for example, the active agent can be mixed with water or othe liquid or liquids, preferably aided by the usage of a surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulation are known in the art and can be employed in implementing the present invention.

The exact concentration of one or more of the compounds of the present invention in a composition thereof with one or a plurality of adjuvants can vary; it is necessary only that one or more of the products be present in such amount as to make possible the application of an inactivating dosage to an insect or arachnid. In many situations, a composition comprising 0.001 percent of the present active agent is effective for the administration of an inactivating amount thereof to insect and arachnid pest organisms. Compositions having a higher concentration of active agent, such as a concentration of from 0.001 to 0.5 percent, can of course be employed. In still other operations, compositions containing from 0.5 to 98 percent by weight of one compound or from 0.5 to 98 percent of a total of more than one compound, are conveniently employed. Such compositions are adapted to be employed as treating compositions and applied to insects and arachnids and to their habitats, or to be employed as concentrates and subsequently diluted with additional adjuvant to produce ultimate treating compositions.

Liquid compositions containing the desired amount of active agent are prepared by dissolving the substance in an organic liquid or by dispersing the substance in water with or without the aid of a suitable surface active dispersing agent such as an ionic or non-ionic emulsifying agent. Such compositions can also contain modifying substances which serve as a "spreader" and "sticker" on plant foliage. Suitable organic liquid carriers include the agricultural spray oils and the petroleum distillates such as diesel fuel, kerosene, fuel oil napthas and Stoddard solvent. Among such liquids the petroleum distillates are generally preferred. The aqueous compositions can contain one or more water immiscible solvents for the toxicant compound. In such compositions, the carrier comprises an aqueous emulsion, e.g., a mixture of water, emulsifying agent and water immiscible solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. For a review of known surface-active agents which are suitably employed in implementing the present invention, attention is directed to U.S. Pat. No. 3,095,299, second column, lines 25–36, and references there cited.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the practices of the present invention. Also, such dust compositions can be dispersed in water, with or without the aid of a dispersing agent, to form spray mixtures.

Also, the compounds of the present invention can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

When operating in accordance with the present invention, one or more of the compounds or a composition containing one or more of the compounds is applied to the pests to be controlled directly, or by means of application to a portion or portions of their habitat in any convenient manner, for example, by means of hand dusters or sprayers or by simple mixing with the food to be ingested by the organisms. Application to the foliage of plants is conveniently carried out with power dusters, boom sprayers, and fog sprayers. In such foliar applications, the employed compositions should not contain any appreciable amounts of any phytotoxic diluents. In large-scale operations, dusts, or low-volume sprays can be applied from an airplane. The present invention also comprehends the employment of compositions comprising one or more of the compounds of the present invention, an adjuvant, and one or more biologically active materials, such as other insecticides, fungicides, miticides, bactericides, nematocides, and the like.

EXAMPLE 47

Compounds evaluated for the control of insects and arachnids, as reported in the following examples, were formulated in accordance with the following procedure. Initially, 55 grams of a mixture of two nonionic sulfonate emulsifiers were mixed with 1 liter of cyclohexanone. Of the resulting mixture, 0.9 milliliter was subsequently further mixed with 90 milligrams of the subject compound and diluted with distilled water to 90 milliliters, containing the subject compound at a concentration of 1000 parts per million. For evaluation at lower concentrations, the mixture was further diluted with a dilution composition consisting of 4 liters of distilled water and a total of 1.8 milliliter of the same two nonionic sulfonate emulsifiers.

The insecticidal and arachnicidal activity of the compounds of this invention is illustrated by the following tests against representative insects and arachnids.

TEST METHODS

Mexican Bean Beetle

Epilachna varivestis (Coleoptera)

Cuttings of four-to-six-day-old Bountiful snap bean plants containing two leaves with approximately 5 square inches of leaf surface each were placed in water. The leaves were sprayed to wetting with about 5–10 ml. of a formulation containing a predetermined level of the test compound. Half of the formulation was sprayed on the top surface and half on the bottom surface of the leaf using a DeVilbiss atomizer at 10 psi held at a distance of about 18 inches from the leaf. After the leaves had dried, they were cut from the stem and placed separately in petri dishes. Ten third instar, non-molting Mexican bean beetle larvae grown on Bountiful snap beans were placed on each leaf. Controls consisted of two leaves sprayed with 5 ml. of 500 ppm. formulation of S-(1,2-dicarbethoxyethyl) 0,0-dimethyl phosphorodithioate (reference standard), two leaves sprayed with the formulation without the active ingredient and two leaves held as untreated controls. After 48 hours, a mortality count was made and the amount of feeding noted. Moribund larvae were counted as dead. The following toxicity rating scale was used;

| Percent Dead | Rating |
|---|---|
| 0–10 | 0 |
| 11–20 | 1 |
| 21–30 | 2 |
| 31–40 | 3 |
| 41–50 | 4 |
| 51–60 | 5 |
| 61–70 | 6 |
| 71–80 | 7 |
| 81–90 | 8 |
| 91–100 | 9 |

SOUTHERN ARMYWORM

Prodenia eridania (Lepidoptera)

Ten uniform Southern armyworm larvae about 1–1.5 cm. in length, grown on Henderson lima beans, were placed on excized bean leaves in petri dishes. The bean leaves were obtained and sprayed with the insecticide in the same way as were the snap bean leaves in the Mexican bean beetle test. The reference standards in this instance were leaves sprayed with 5 ml. of 100 ppm. DDT solution. Mortality counts were made 48 hours after spraying and again moribund larvae were counted as dead. Missing larvae which had probably been eaten were considered alive. The same rating scale was used as in the Mexican bean beetle test.

TWO-SPOTTED SPIDER MITE

Tetranychus urticae (Acarina)

Two-spotted spider mites were raised on green bean plants, then transferred to squash plants. The squash plants were maintained for two days so that the infestation was well established. The infected squash plants were then sprayed with a test formulation containing the subject compound as in the preceding test methods. Mortality was determined by estimation 48 hours after spraying. The same rating scale was used as in other test procedures.

MILKWEED BUG

Oncopelitis fasciatus (Hemiptera)

Ten adult milkweed bugs were chilled and placed in a test cage. The cages containing the bugs were sprayed with 5 ml. of a test formulation containing a pre-determined amount of the insecticide, using a DeVilbiss atomizer at 10 psi held 33 inches from the top of the cage. After the cage had been allowed to dry, the bugs were fed and watered for 48 hours. A formulation containing 500 ppm. of S-(1,2-dicarbethoxyethyl) 0,0-dimethyl phosphorodithioate was used as a reference standard and two unsprayed cages were kept as controls. Mortality counts were made 48 hours after spraying. Moribund adults were considered dead. The same rating scale was employed as before.

HOUSE FLY

Musca domestica (Diptera)

Rearing cages containing four-day-old adult house flies were chilled at 35°–40°F. for about 1 hour. One hundred flies were transferred from the rearing cage to each test cage using a small scoop. The caged flies were kept for 1–2 hours at 70°–80°F. The cages were sprayed in the same manner as described for the milkweed bug with 5 ml. of the test formulation. Two unsprayed cages were held as controls and two cages were sprayed with a 50 ppm. DDT formulation as a reference standard. Mortality counts were made 24 hours after spraying. All flies that did not fly or did not walk up from the bottom of the cage were considered moribund. The same rating scale was employed as heretofore.

BOLL WEEVIL

Anthonomus grandis (Coleoptera)

The procedure was identical to that employed for the Mexican bean beetle and the Southern armyworm, except that 10 adult boll weevils were placed on cotton leaves that had been dipped into formulations of the test compounds. The same rating scale was used.

Test Results

Example 48

EVALUATION OF COMPOUNDS AGAINST MEXICAN BEAN BEETLE

Various compounds of the present invention were evaluated in accordance with the test method described above against Mexican Bean Beetle. The compounds so evaluated, the rates employed, and the results of the evaluations are as set forth in the following table. When more than one evaluation was carried out at a given rate, the result reported for that rate is an average of the several results.

TABLE II

| Compound | Rate in Parts Per Million | Toxicity Rating Against Mexican Bean Beetle |
|---|---|---|
| 4-ethoxy-7-nitro-2,5-bis-(trifluoromethyl)benzimidazole | 1000 | 9.0 |
|  | 500 | 9.0 |
|  | 250 | 9.0 |
|  | 100 | 9.0 |
|  | 50 | 9.0 |
|  | 25 | 8.5 |
|  | 10 | 8.0 |
| 4-ethoxy-7-nitro-5-trifluoromethyl-2-pentafluoroethylbenzimidazole | 1000 | 9.0 |
|  | 500 | 9.0 |
|  | 250 | 9.0 |
|  | 100 | 9.0 |
|  | 50 | 9.0 |
|  | 25 | 9.0 |
| 4-propoxy-7-nitro-5-trifluoromethyl-2-pentafluoroethylbenzimidazole | 1000 | 9.0 |
|  | 500 | 9.0 |
|  | 250 | 5.0 |
|  | 100 | 8.5 |
|  | 50 | 9.0 |
| 4-methoxy-7-nitro-2,5-bis-(trifluoromethyl)benzimidazole | 1000 | 9.0 |
|  | 500 | 4.5 |
|  | 250 | 9.0 |
|  | 100 | 9.0 |

TABLE II-continued

| Compound | Rate in Parts Per Million | Toxicity Rating Against Mexican Bean Beetle |
|---|---|---|
| | 50 | 8.5 |
| 4-propylamino-7-nitro-2,5-bis(trifluoromethyl)benzimidazole | 1000 | 9.0 |
| | 500 | 9.0 |
| | 250 | 9.0 |
| | 100 | 9.0 |
| | 50 | 9.0 |
| 4-piperidino-7-nitro-2,5-bis(trifluoromethyl)benzimidazole | 1000 | 9.0 |
| | 500 | 8.5 |
| | 250 | 8.5 |
| | 100 | 9.0 |
| | 50 | 9.0 |
| | 25 | 9.0 |
| 4-butylamino-7-nitro-2,5-bis(trifluoromethyl)benzimidazole | 1000 | 9.0 |
| | 500 | 9.0 |
| | 250 | 8.5 |
| | 100 | 7.5 |
| 4-cyclohexylamino-7-nitro-2,5-bis(trifluoromethyl)-benzimidazole | 1000 | 9.0 |
| | 500 | 9.0 |
| | 250 | 9.0 |
| | 100 | 8.5 |
| 4-sec-butylamino-7-nitro-2,5-bis(trifluoromethyl)-benzimidazole | 1000 | 9.0 |
| | 500 | 9.0 |
| | 250 | 9.0 |
| 4-propylamino-7-nitro-5-cyano-2-trifluoromethyl-benzimidazole | 1000 | 7.5 |
| | 500 | 9.0 |
| | 250 | 9.0 |
| 4-piperidino-7-nitro-5-cyano-2-pentafluoroethyl-benzimidazole | 1000 | 8.5 |
| | 500 | 9.0 |
| | 250 | 9.0 |
| | 100 | 7.5 |

EXAMPLE 49:

EVALUATION OF COMPOUNDS AGAINST SOUTHERN ARMYWORM

Various compounds of the present invention were evaluated in accordance with the test method described above against Southern Armyworm. The compounds so evaluated, the rates employed, and the results of the evaluation are as set forth in the following table. Where more than one evaluation was carried out at a given rate, the result reported for that rate is an average of the several results.

TABLE III

| Compound | Rate in Parts Per Million | Toxicity Rating Against Southern Armyworm |
|---|---|---|
| 4-ethoxy-7-nitro-2,5-bis-(trifluoromethyl)benzimidazole | 1000 | 9.0 |
| | 500 | 9.0 |
| | 250 | 9.0 |
| | 100 | 9.0 |
| | 50 | 8.5 |
| 4-ethoxy-7-nitro-5-trifluoromethyl-2-pentafluoroethylbenzimidazole | 1000 | 9.0 |
| | 500 | 9.0 |
| | 250 | 9.0 |
| | 100 | 9.0 |
| | 50 | 9.0 |
| 4-propoxy-7-nitro-5-trifluoromethyl-2-pentafluoroethylbenzimidazole | 1000 | 9.0 |
| | 500 | 9.0 |
| | 250 | 9.0 |
| | 100 | 9.0 |
| | 50 | 8.5 |
| 4-methoxy-7-nitro-2,5-bis-(trifluoromethyl)benzimidazole | 1000 | 9.0 |
| | 500 | 9.0 |
| | 250 | 8.0 |
| | 100 | 9.0 |
| 4-propylamino-7-nitro-2,5-bis(trifluoromethyl)benzimidazole | 1000 | 9.0 |
| | 500 | 9.0 |
| | 250 | 9.0 |
| | 100 | 8.5 |
| 4-butylamino-7-nitro-2,5-bis(trifluoromethyl)benzimidazole | 1000 | 9.0 |
| | 500 | 9.0 |
| | 250 | 9.0 |
| 4-cyclohexylamino-7-nitro-2,5-bis(trifluoromethyl)-benzimidazole | 1000 | 9.0 |
| | 500 | 9.0 |
| 4-sec-butylamino-7-nitro-2,5-bis(trifluoromethyl)-benzimidazole | 1000 | 9.0 |
| | 500 | 9.0 |
| | 250 | 9.0 |

TABLE III-continued

| Compound | Rate in Parts Per Million | Toxicity Rating Against Southern Armyworm |
|---|---|---|
| | 100 | 9.0 |
| 4-propylamino-7-nitro-5-cyano-2-trifluoromethyl-benzimidazole | 1000 | 9.0 |
| | 500 | 9.0 |
| | 250 | 8.5 |
| 4-piperidino-7-nitro-5-cyano-2-pentafluoroethyl-benzimidazole | 1000 | 9.0 |
| | 500 | 9.0 |
| | 250 | 9.0 |
| | 100 | 7.5 |

EXAMPLE 50:

EVALUATION OF COMPOUNDS AGAINST TWO-SPOTTED SPIDER MITE

Various compounds of the present invention were evaluated in accordance with the test method described above against Two-spotted Spider Mite. The compounds so evaluated, the rates employed, and the results of the evaluation are as set forth in the following table.

TABLE IV

| Compound | Rate in Parts per Million | Toxicity Rating Against Two-Spotted Spider Mite |
|---|---|---|
| 4-ethoxy-7-nitro-2,5-bis(trifluoromethyl)-benzimidazole | 1000 | 9.0 |
| | 500 | 9.0 |
| | 250 | 9.0 |
| | 100 | 9.0 |
| | 50 | 9.0 |
| | 25 | 9.0 |
| | 10 | 9.0 |
| 4-ethoxy-7-nitro-5-trifluoromethyl-2-pentafluoroethylbenzimidazole | 1000 | 9.0 |
| | 500 | 9.0 |
| | 250 | 9.0 |
| | 100 | 9.0 |
| | 50 | 9.0 |
| | 25 | 9.0 |
| | 10 | 8.0 |
| 4-propoxy-7-nitro-5-trifluoromethyl-2-pentafluoroethylbenzimidazole | 1000 | 9.0 |
| | 500 | 9.0 |
| | 250 | 9.0 |
| | 100 | 9.0 |
| | 50 | 9.0 |
| | 25 | 8.5 |
| | 10 | 9.0 |
| 4-methoxy-7-nitro-2,5-bis-(trifluoromethyl)benzimidazole | 1000 | 9.0 |
| | 500 | 9.0 |
| | 250 | 9.0 |
| | 100 | 9.0 |
| | 50 | 9.0 |
| | 25 | 9.0 |
| | 10 | 9.0 |
| 4-ethylthio-7-nitro-2,5-bis-(trifluoromethyl)benzimidazole | 500 | 9.0 |
| | 250 | 9.0 |
| | 100 | 8.5 |
| 4-propylamino-7-nitro-2,5-bis(trifluoromethyl)benzimidazole | 1000 | 9.0 |
| | 500 | 9.0 |
| | 250 | 9.0 |
| | 100 | 9.0 |
| | 50 | 9.0 |
| | 25 | 9.0 |
| 4-sec-butylamino-7-nitro-2,5-bis(trifluoromethyl)-benzimidazole | 1000 | 9.0 |
| | 500 | 9.0 |
| | 250 | 9.0 |
| | 100 | 9.0 |

EXAMPLE 51:

EVALUATION OF COMPOUNDS AGAINST MILKWEED BUG

Various compounds of the present invention were evaluated in accordance with the test method described above against Milkweed Bug. The compounds so evaluated, the rates employed and the results of the evaluation are as set forth in the following table.

TABLE V

| Compound | Rate in Parts per Million | Toxicity Rating Against Milkweed Bug |
|---|---|---|
| 4-ethoxy-7-nitro-2,5-bis-(trifluoromethyl)benzimidazole | 1000 | 9.0 |
| | 500 | 9.0 |
| | 250 | 9.0 |
| | 100 | 9.0 |
| | 50 | 9.0 |
| | 25 | 9.0 |
| | 10 | 8.5 |
| 4-ethoxy-7-nitro-5-trifluoromethyl-2-pentafluoroethyl-benzimidazole | 1000 | 9.0 |
| | 500 | 9.0 |
| | 250 | 9.0 |
| 4-propoxy-7-nitro-5-trifluoromethyl-2-pentafluoroethyl-benzimidazole | 1000 | 9.0 |
| | 500 | 9.0 |
| 4-methoxy-7-nitro-2,5-bis-(trifluoromethyl)benzimidazole | 1000 | 9.0 |
| | 500 | 9.0 |
| | 250 | 9.0 |
| | 100 | 9.0 |
| 4-ethylthio-7-nitro-2,5-bis-(trifluoromethyl)benzimidazole | 500 | 9.0 |
| | 250 | 9.0 |
| | 100 | 9.0 |
| 4-sec-butylamino-7-nitro-2,5-bis(trifluoromethyl)benzimidazole | 1000 | 9.0 |
| | 500 | 9.0 |
| | 250 | 9.0 |
| | 100 | 8.0 |

EXAMPLE 52:

EVALUATION OF COMPOUNDS AGAINST HOUSE FLY

Various compounds of the present invention were evaluated in accordance with the test method described above against House Fly. The compounds so evaluated, the rates employed, and the results of the evaluations are as set forth in the following table. Where more than one evaluation was carried out, the result reported for that rate is an average of the several results.

TABLE VI

| Compound | Rate in Parts per Million | Toxicity Rating Against House Fly |
|---|---|---|
| 4-ethoxy-7-nitro-2,5-bis-(trifluoromethyl)benzimidazole | 1000 | 9.0 |
| | 500 | 9.0 |
| | 250 | 9.0 |
| 4-ethoxy-7-nitro-5-trifluoromethyl-2-pentafluoroethylbenzimidazole | 1000 | 8.0 |
| | 500 | 8.5 |
| | 250 | 9.0 |
| | 100 | 9.0 |
| | 50 | 9.0 |
| | 25 | 9.0 |
| 4-propoxy-7-nitro-5-trifluoromethyl-2-pentafluoroethylbenzimidazole | 1000 | 9.0 |
| | 500 | 9.0 |
| | 250 | 9.0 |
| | 100 | 8.5 |
| | 50 | 7.5 |
| 4-ethoxy-7-nitro-5-cyano-2-trifluoromethylbenzimidazole | 1000 | 9.0 |
| | 500 | 9.0 |
| | 250 | 8.5 |
| | 100 | 8.0 |
| 4-methoxy-7-nitro-2,5-bis-(trifluoromethyl)benzimidazole | 1000 | 9.0 |
| | 500 | 9.0 |
| | 250 | 9.0 |
| | 100 | 9.0 |
| | 50 | 9.0 |
| 4-propylamino-7-nitro-2,5-bis(trifluoromethyl)benzimidazole | 1000 | 9.0 |
| | 500 | 9.0 |
| | 250 | 9.0 |
| | 100 | 9.0 |
| 4-sec-butylamino-7-nitro-2,5-bis(trifluoromethyl)-benzimidazole | 1000 | 9.0 |
| | 500 | 9.0 |
| | 250 | 9.0 |
| | 100 | 7.5 |

EXAMPLE 53:

EVALUATION OF COMPOUNDS AGAINST BOLL WEEVIL

Various compounds of the present invention were evaluated in accordance with the test method described above against Boll Weevil. The compounds so evaluated, the rates employed, and the results of the evaluations are as set forth in the following table. Where more than one evaluation was carried out, the result reported for that rate is an average of the several results.

TABLE VII

| Compound | Rate in Parts per Million | Toxicity Rating Against Boll Weevil |
|---|---|---|
| 4-ethoxy-7-nitro-5-trifluoromethyl-2-pentafluoroethylbenzimidazole | 1000 | 9.0 |
| | 500 | 9.0 |
| | 250 | 9.0 |
| | 100 | 8.5 |
| | 50 | 9.0 |
| 4-propoxy-7-nitro-5-trifluoromethyl-2-pentafluoroethylbenzimidazole | 1000 | 9.0 |
| | 500 | 9.0 |
| | 250 | 9.0 |
| 4-ethoxy-7-nitro-5-cyano-2-trifluoromethylbenzimidazole | 1000 | 8.5 |
| | 500 | 8.5 |
| | 250 | 8.5 |
| | 100 | 9.0 |
| | 50 | 8.0 |
| 4-methoxy-7-nitro-2,5-bis-(trifluoromethyl)benzimidazole | 1000 | 8.5 |
| | 500 | 9.0 |
| | 250 | 9.0 |
| 4-propylamino-7-nitro-2,5-bis(trifluoromethy)benzimidazole | 1000 | 9.0 |
| | 500 | 9.0 |
| | 250 | 9.0 |
| | 100 | 9.0 |
| | 50 | 9.0 |
| 4-propylamino-7-nitro-5-cyano-2-trifluoromethylbenzimidazole | 1000 | 8.0 |
| | 500 | 9.0 |
| | 250 | 9.0 |
| | 100 | 7.5 |
| 4-piperidino-7-nitro-5-cyano-2-pentafluoroethylbenzimidazole | 1000 | 8.0 |
| | 500 | 8.5 |
| | 250 | 8.5 |

Certain of the compounds of the present invention exhibit herbicidal activity. This activity is most pronounced in the compounds wherein X represents trifluoromethyl and Z represents an alkoxy group, such as loweralkoxy of $C_1$–$C_4$. In employing these compounds as insecticides for the control of insects which attack plants, due regard should be paid to the selection of rates, the growth stage of plants, the susceptibility of the plants to the compounds, and the like, in order that the insecticidal effect be achieved with little or no undesired herbicidal effect. When it is desired to utilize the herbicidal activity of the compounds, the compounds can be employed to control plant growth generally, or selectively to control weeds growing in crop plants. The compounds exhibit herbicidal activity at rates of from ½ lb. or less to 10 lbs. or more, per acre.

When employed as herbicides, the compounds are conveniently formulated with adjuvants. Reference is made to the discussion hereinabove regarding the formulation of the compounds incident to utilization as insecticides. The compounds can be applied pre-emergent or post-emergent, in accordance with conventional modes of application.

Representative compounds were evaluated for herbicidal activity. Uniformly the evaluation was conducted by dispersing the respective compound with suitable surfaceactive agents in an aqueous solution and spraying the solution onto plots seeded with various species. A control plot was sprayed with an aqueous solution containing only the surfaceactive agents, in the same concentration. The plots were held under good growing conditions for twelve to thirteen days and then examined.

When evaluated by this method at a rate of 2 pounds/acre, 4-methoxy-7-nitro-2,5-bis(trifluoromethyl)benzimidazole gave essentially complete control of crabgrass, pigweed, and foxtail, without any phytotoxic effect on corn, cotton, or soybeans. Essentially, the same results were obtained with 4-ethoxy-7-nitro-2,5-bis(trifluoromethyl)benzimidazole and with 4-propoxy-7-nitro-5-trifluoromethyl-2-pentafluoroethyl-benzimidazole, each at 4 pounds per acre.

Preferred compounds of the present invention are those of the formula

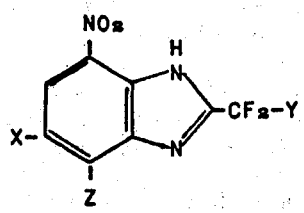

wherein X and Y have the same meanings as set forth above, and Z' represents loweralkoxy of $C_{1-4}$, cycloalkoxy of $C_5$-$C_6$, cycloalkylamino of $C_5$-$C_6$, loweralkylamino of $C_1$-$C_4$, or diloweralkylamino wherein each loweralkyl is of $C_1$-$C_4$ but both loweralkyl groups together do not contain more than a total of 6 carbon atoms. Preferred X and Y groups are $CF_3$ and F, respectively.

The compounds to be employed as starting materials in accordance with the present invention:

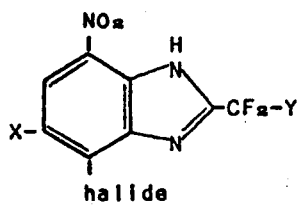

are readily prepared by either of two synthetic routes.

In one synthetic route, a compound of the formula

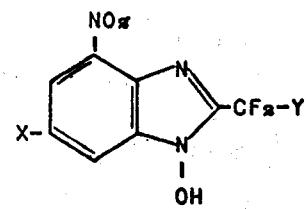

is treated with a halide-containing nucleophilic reagent, such as HCl, HBr, phosphorus oxychloride, phosphorus oxybromide, phosphorus thiochloride, phosphorus tribromide, phosphorus trichloride, thionyl chloride, thionyl bromide, or the like.

The reaction conditions are not critical. In general, the reaction is more conveniently carried out in an inert liquid as reaction medium. Suitable such liquids include ethers, such as diethyl ether and tetrahydrofuran; hydrocarbons; and acetone. Where any of the phosphorus halides or thionyl halides is employed as nucleophile, use of a small amount of dimethylformamide, to constitute a Vilsmeier-Haack reagent, is preferred. The reaction goes forward under a wide range of temperatures, such as from 0° to 150°. Generally, however, there is no advantage to the use of temperatures other than room temperatures. The reaction consumes the 1-hydroxy compound and the nucleophilic reagent in amounts representing equimolecular proportions. Separation, and if desired, purification, are carried out in conventional procedures.

In representative procedures, 1-hydroxy-4-nitro-2,6-bis(trifluoromethyl)benzimidazole (3.3 grams) was mixed at room temperature with 50 milliliters of thionyl chloride, and 0.5 milliliter of dimethylformamide was added. The reaction mixture was stirred for 1 hour, then poured slowly into cold water, the desired product precipitated and was separated by filtration. TLC in ether showed a spot running faster than the starting material, NMR showed one aromatic peak, and a Beilstein test gave a green flame, indicating the presence of halogen. After recrystallization from a mixture of benzene and an aliphatic hydrocarbon fraction (Skellysolve B), the product melted at 180°–83°C. Analysis, Calc.: C, 32.4; H, .60; N, 12.6; Cl, 10.63 Found: C, 32.6; H, .89; N, 12.45; Cl, 10.75

In addition to the foregoing method, the starting bromides can also be prepared in accordance with the following reaction sequence:

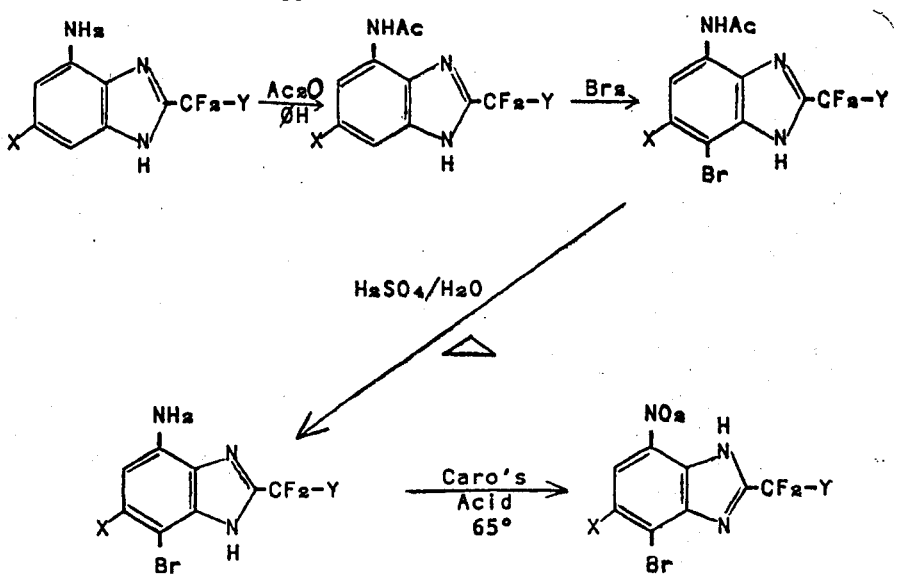

Each of the reactions is carried out in known procedures.

We claim:
1. Compound of the formula

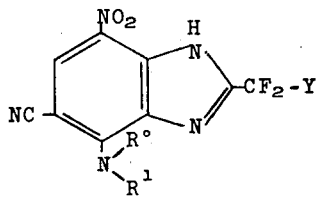

wherein Y represents
  a. hydrogen,
  b. chlorine,
  c. fluorine,
  d. trifluoromethyl, or
  e. pentafluoroethyl;

and wherein $R^o$ and $R_1$ are either taken separately, in which case each independently represents one of the following, subject to the limitation that at least one of $R^o$ and $R^1$ contains more than 1 carbon atom and that $R^o$ and $R^1$ together contain less than 9 carbon atoms:
  1. hydrogen
  2. alkyl
  3. alkenyl containing more than 2 carbon atoms,
  4. alkynyl containing more than 2 carbon atoms,
  5. (fluoroalkyl)methyl wherein alkyl is $C_1$-$C_7$, both inclusive, and bears at least one fluorine atom,
  6. cycloalkyl of $C_3$-$C_8$, both inclusive
  7. cycloalkylloweralkyl, wherein cycloalkyl is of $C_3$-$C_6$, both inclusive, and loweralkyl is of $C_1$-$C_4$, both inclusive, or
  8. loweralkylcycloalkyl, wherein cycloalkyl and loweralkyl are as defined in the preceding candidate moiety;

or $R^o$ and $R^1$ are taken together, in which case they jointly constitute, with the nitrogen atom to which they are attached, piperidino; and the alkali metal and alkaline earth metal salts thereof.

2. The compound of claim 1 which is 4-propylamino-7-nitro-5-cyano-2-trifluoromethylbenzimidazole.

3. The compound of claim 1 which is 4-piperidino-7-nitro-5-cyano-2-pentafluoroethylbenzimidazole.

4. The compound of claim 1 which is 4-(diallylamino)-7-nitro-5-cyano-2-difluorochloromethylbenzimidazole.

5. The compound of claim 1 which is 4-(2-cyclohexylethylamino)-7-nitro-5-cyano-2-pentafluoroethylbenzimidazole.

6. The compound of claim 1 which is 4-piperidino-7-nitro-5-cyano-2-trifluoromethylbenzimidazole.

7. The compound of claim 1 which is 4-(N-methylcyclopentylamino)-7-nitro-5-cyano-2-trifluoromethylbenzimidazole.

8. The compound of claim 1 which is 4-cydopentanemethylamino-7-nitro-5-cyano-2-trifluoromethylbenzimidazole.

9. The compound of claim 1 which is 4-((2-ethylcyclobutyl)amino)-7-nitro-5-cyano-2-trifluoromethylbenzimidazole.

* * * * *